US006891086B2

(12) United States Patent
Chaudhuri et al.

(10) Patent No.: US 6,891,086 B2
(45) Date of Patent: May 10, 2005

(54) PLASTID TRANSFORMATION OF *BRASSICA*

(75) Inventors: Sumita Chaudhuri, Cary, NC (US); Janette V. Oakes, Davis, CA (US)

(73) Assignee: Calgene LLC, Davis, CA (US)

( * ) Notice: Subject to any disclaimer, the term of this patent is extended or adjusted under 35 U.S.C. 154(b) by 288 days.

(21) Appl. No.: 10/219,227

(22) Filed: Aug. 15, 2002

(65) Prior Publication Data

US 2003/0106094 A1 Jun. 5, 2003

Related U.S. Application Data

(62) Division of application No. 09/465,856, filed on Dec. 17, 1999, now abandoned, which is a continuation of application No. 09/220,557, filed on Dec. 23, 1998, now Pat. No. 6,515,206.

(51) Int. Cl.[7] ........................ C12N 15/82; C12N 15/12; C12N 15/31; A01N 5/00; A01N 5/10

(52) U.S. Cl. ........................ 800/306; 800/278; 800/287; 800/288; 800/302; 435/69.4; 435/69.5; 435/69.51; 435/69.52; 435/69.6; 435/419

(58) Field of Search ................ 800/278, 287, 800/288, 302, 306; 435/69.4–69.6, 419

(56) References Cited

U.S. PATENT DOCUMENTS

| | | | |
|---|---|---|---|
| 4,810,648 A | 3/1989 | Stalker | |
| 4,956,282 A | 9/1990 | Goodman et al. | |
| 5,094,945 A | 3/1992 | Comai | |
| 5,420,034 A | 5/1995 | Kridl et al. | |
| 5,451,513 A | 9/1995 | Maliga et al. | |
| 5,545,817 A | 8/1996 | McBride et al. | |
| 5,576,198 A | 11/1996 | McBride et al. | |
| 5,608,152 A | 3/1997 | Kridl et al. | |
| 5,627,061 A | 5/1997 | Barry et al. | |
| 5,633,435 A | 5/1997 | Barry et al. | |
| 5,693,507 A | 12/1997 | Daniell et al. | |

FOREIGN PATENT DOCUMENTS

| | | |
|---|---|---|
| GB | 2 183 660 | 6/1987 |
| WO | WO 92/15675 | 9/1992 |
| WO | WO 95/16783 | 6/1995 |
| WO | WO 97/32977 | 9/1997 |
| WO | WO 98/06862 | 2/1998 |
| WO | WO 99/05265 | 2/1999 |

OTHER PUBLICATIONS

Pang et al. Gene 116: 165–172 (1992).*
Dandekar et al. Plant Science 96(1–2): 151–162 (1994).*
Bilang et al., Containing excitement over transplastomic plants, *Nature Biotechnology* 16 333–334 (1998).
Blowers et al., Studies on *Chlamydomonas* chloroplst transformation: Foreign DNA can be stably maintained in the chromosome *The Plant Cell 1* :123–132 (1989).

Boynton et al., Chloroplast transformation in *Chlamydomonas* with high veloctiy microprojectiles, *Science 240*:1534–1538 (1988).

Broun et al., A bifunctional oleate 12–hydroxylase: desaturase from *esquerella fendleri*, *The Plant Journal 13*:201–210 (1998).

Carrer et al., Targeted insertion of foreign genes into the tobacco plastid genome without physical linkage to the selectable marker gene. *Bio/technology*, 13:791–794 (1995).

Daniell et al., Containment of herbicide resistance through genetic engineering of the chloroplast genome, *Nature Biotechnology 16*:345–348 (1998).

Daniell et al., Foreign gene expression in chloroplasts of higher plants mediated by tungsten particle bombardment, *Methods in Enzymology 217*:536–557 (1993).

Daneill et al., Uptake and expression of bacterial and cyanobacterial genes by isolated cyanobacterial genes by isolated cucumber etioplasts *PNAS USA 84*:6349–6353 (1987).

DeBlock et al., Engineering herbicide resistance in plants by expression of a detoxifying enzyme, *The EMBO Journal 6*:2513–2518 (1987).

DeBlock et al., Chloroplast transformation by *Agrobacterium tumefaciens*, *The EMBO Journal 4*: 1367–1372 (1985).

Dunwell *In vitro* regeneration from excised leaf discs of three *Brassica* species. *I of Experimental Botany*, 3(129):789–799 (1981).

Golds et al. Stable plastid transformation in PEG–treated protoplasts of *Nicotiana tabacum. Bio/technology*, 11:95–97 (1993).

Gray et al., Reducing transgene escape routes, *Natures 392*:653–653 (1998).

Herrera–Estrella et al.,Light–inducible and chlorplast–associated expression of a chimaeric gene introduced in Nicotiana tabacum using a Ti plasmid vector, *Nature 310*:115–120 (1984).

Herrera–Estrella et al., Expression of chimaeric genes tranferred into plant cells using a Ti–plasmid–derived vector, *Nature 303*:209–213 (1983).

(Continued)

Primary Examiner—David T. Fox
(74) Attorney, Agent, or Firm—M. Todd Rands

(57) ABSTRACT

A method is provided for transforming *Brassica* plants to express DNA sequences of interest from the plant cell plastid. The method allows the transformation of *Brassica* plant tissue with heterologous DNA constructs. Such DNA constructs comprise, in the 5' to 3' direction of transcription, a promoter region functional in a plant plastid and a DNA sequence of interest. The invention further provides for *Brassica* cells in which the plastids contain heterologous DNA constructs.

24 Claims, 3 Drawing Sheets

OTHER PUBLICATIONS

Hiratsuka et al. The complete sequence of the rice (*Orzaya sativa*) chloroplast genome: Intermolecular recombination between distinct tRNA genes accounts for a major plastid DNA inversion during the evolution of the cereals. *Mol. Gen. Genet.* 217:185–194 (1989).

Horsch et al., A simple and general method for transferring genes into plants, *Science* 227:1229–1231 (1985).

Klein et al., Transformation of microbes, plants and animals by particle bombardment, *Bio/Technology* 10:286–291 (1992).

Leung et al., Growth hormone receptor and serum binding protein: purification, cloning and expression, *Nature* 330:537–543 (1987).

Maliga, Towards plastid transformation in flowering plants. *Trends in Biotech.* 11:101–107 (1993).

McBride et al., Controlled expression of plastid transgenes in plants based on a nuclear DNA–encoded and plastid–targeted T7 RNA polymerase, *PNAS USA* 91:7301–7305 (1994).

McBride et al., Amplification of a chimeric *Bacillus* gene in chloroplasts leads to an extraordinary level of insecticidal protein in tobacco. *Bio/Technology* 13:362–365 (1995).

Medgyesy, Selection and Analysis of Cytoplasmic Hybrids, *In:Plant Cell Line Selection, P. Dix, ed., VCH:Weinheim,* pp. 307–313(1990).

Misawa et al., Expression of an Erwinia phytoene desaturase gene not only confers multiple resistace to herbicides interfering with carotenoid biosynthesis but also alters xanthophylls metabolism in transgenic plants, *The Plant Journal* 6:481–489 (1994).

Misawa et al., Functional expression of the *Erwinia uredovora* carotenoid biosynthesis gene crtI in transgenic plants showing an increase of β–carotene biosynthesis activity and resistance to the bleaching herbicide nonflurazon, *The Plant Journal* 4:833–840 (1993).

Murad, *Pharmacological Basis or Therapeutics*, 8$^{th}$ edition, Section XV, Pergaman Press 1332–1360 (1990).

Nicoll et al., Structural features of prolactins and growth hormones that can be related to their biological properties, *Endoctrine Reviews* 7:169–213 (1986).

Ohymara et al. Chloroplast gene organization deduced from complete sequence of liverwort *Marchantia polymorpha* chloroplast DNA. *Nature* 322:572–574 (1986).

O'Neill et al. Chloroplast transformation in plants: polyethylene glycol (PEG) treatment of protoplasts is and alternative to biolistic delivery systems. *Plant Journal* 3(5):729–738 (1993).

Padgette et al., *Herbicide–Resistant Crops,* Chapter 4, CRC Press, Inc., 53–88 (1996).

Palmer et al., *In: Arabidopsis, Meyerowitz et al., eds., Cold Spring Harbor Lab. Press: Cold Spring Harbor,* pp. 37–63 (1994).

Penaloza–Vazquez et al., Expression of the hygromycin B phosphotransferase gene confers tolerance to the herbicide glyphosate, *Plant Cell Reports* 14:482–487 (1995).

Pilon–Smits et al. Overexpression of ATP sulfurylase in Indian Mustard leads to increased selenate uptake, reductions, and tolerance. *Plant Physiology* 119:123–132 (1999).

Radke et al., Transformation of *Brassica napus* L. using *Agrobacterium tumefaciens*: developmentally regulated expression of a reintroduced napin gene, *Theoretical and Applied Genetics* 75:685–694 (1988).

Radke et al., Transformation and regeneration of *Brassica rapa* using *Agrobacterium tumefaciens, Plant Cell Reports* 11:499–505 (1992).

Roesler et al. Targeting of the Arabidopsis homomeric acetyl–coenzyme A carboxylast to plastids of rapeseeds. *Plant Physiology* 113(1)75–81 (1997).

Romer et al., Expression of the genes encoding the early carotenoid biosynthetic enzymes in *Capsicum annuum, Biochemical and Biophysical Research Communications* 196: 1414–1421 (1993).

Rose et al. Introns act post–transcriptionally to increase expression of the *Arabidopsis thaliana* tryptophan pathway gene PAT1. *Plant Journal* 11(3):455–464 (1997).

Sanford et al. Optimizing the biolistic process for different biological applications. *Methods in Enzymology* 217:483–509 (1993).

Sathasivan et al., Nucleotide sequence of a mutant acetolactate synthase gene from an imidazolinone–resistant *Arabidopsis thaliana* var. Columbia, *Nucleic Acids Research* 18:2188 (1990).

Shinozaki et al.. The complete nucleotide sequence of the tobacco chloroplast genome: its gene organization and expression. *EMBO J.* 5:2043–2049 (1986).

Sikdar et al. Plastid transformation in *Arabidopsis thaliana, Plant Cell Reports* 18:20–24 (1998).

Slocombe et al., Temporal and tissue–specific regualtion of a *Brassica napus* stearoyl–acyl carrier protein desaturase gene, *Plant Physiology* 104:1167–1176 (1994).

Stalker et al., Purification and properties of a nitrilase specific for the herbicide bromoxynil and corresponding nucleotide sequence analysis of the *bxn* gene, *The Journal of Biological Chemistry* 263:6310–6314 (1988).

Stalker et al., A single amino acid substitution in the enzyme 5–enolpyruvylshikimate–3–phosphate synthase confers resistance to the herbicide glyphosate, *The Journal of Biological Chemistry* 260:4724–4728 (1985).

Staub et al. Accumulation of D1 polypeptide in tobacco plastids is regulated via the untranslated region of the *psbA* mRNA. EMBO J. 12(2)601–606 (1993).

Staub et al., Expression of a chimeric midA gene indicates that polycistronic mRNAs are efficiently translated in tobacco plastids, The Plant Journal 7:845–848 (1995).

Stringam, Regenration of Leaf–Callus Cultures of Haploid Rapeseed (*Brassica napus* L.), Z., *Pflanzenphysiol.* 92:459–462 (1979).

Svab et al. Stable transformation of plastids in higher plants. *Proc. Natl. Acad. Sci. USA* 87:8526–8530 (1990).

Svab et al. High–frequency plastid transformation in tobacco by selection for a chimeric aadA gene. *Proc. Natl. Acad. Sci. USA* 90:913–917 (1993).

Tsien, The green fluorescent protein, *Annual Review of Biochemistry* 67:509–544 (1998).

Valentin et al. PHA production from bacteria to plants. *International J of Biological Macromolecules.* 25:303–306 (1999).

Welsh et al., Fingerprinting genomes using PCR with arbitrary primers, *Nucleic Acids Research* 18:7213–7218 (1990).

Ye et al. Optimization of delivery of foreign DNA into higher–plant chloroplasts. *Plant Molecular Biology* 15:809–819 (1990).

Zoubenko et al. Efficient targeting of foreign genes into the tobacco plastid genome. *Nucleic Acids Research* 22(19) 3819–3824 (1994).

* cited by examiner

SEQUENCE LISTING

<160> NUMBER OF SEQ ID NOS: 19

<210> SEQ ID NO 1
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 1
agggagacca caacggtttc cctctagaaa taattttgtt taactttaag aaggagatat    60
acc                                                                  63

```
<210> SEQ ID NO 2
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 2
ggtatatctc cttcttaaag ttaaacaaaa ttatttctag agggaaaccg ttgtggtctc      60
cct                                                                   63

<210> SEQ ID NO 3
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 3
actgggtacc cgagtgaata gaaagttgga tctacattg                            39

<210> SEQ ID NO 4
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 4
actgctcgag gcgcgccgac aattgaatcc aacttttttcc attattt                   47

<210> SEQ ID NO 5
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 5
actggcggcc gcaactactc ctatcggaaa taggattgac ta                        42

<210> SEQ ID NO 6
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 6
catggagctc gatctccctc caaaccgtac atacgact                             38

<210> SEQ ID NO 7
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 7
gatcgaattc atttaattaa ttatatttct atgtatatag attcgtttat aa             52

<210> SEQ ID NO 8
<211> LENGTH: 36
<212> TYPE: DNA
<213> ORGANISM: Artificial Sequence
<220> FEATURE:
```

```
<223> OTHER INFORMATION: Synthetic Oligonucleotide

<400> SEQUENCE: 8
gatcccatgg taaaatcctt ggtttatttta atcatc                               36

<210> SEQ ID NO 9
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 9
gatcgagctc tacaaataat gatctagatt ctttagtgtt agtctatacc tagt            54

<210> SEQ ID NO 10
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 10
gatcaagctt aggcggccgc acgcagcaat attttttttg ataa                       44

<210> SEQ ID NO 11
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 11
gatcggatcc aaggccggcc gacttgctcc ctcgctgtga tcgaataag                  49

<210> SEQ ID NO 12
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 12
tttctagtgg gaaaccgttg tggtctccct acaaagctga ttcggaattg tctttc          56

<210> SEQ ID NO 13
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 13
cgatacttcg gcgatcaccg cttcccttcc catgggtata tctccttctt aaagtt          56

<210> SEQ ID NO 14
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 14
gatcttctag aactataaaa aagaggatgt taaagactca tatatagctt g               51
```

```
<210> SEQ ID NO 15
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 15
gatcgagctc atggcgcgcc attttatata ttttctatac aataattcta tac       53

<210> SEQ ID NO 16
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 16
agaaggagat atacccatgg gaagggaagc ggtgatcgc                        39

<210> SEQ ID NO 17
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 17
acgttctaga attatttgcc gactacctta gtgatctcg                        39

<210> SEQ ID NO 18
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 18
tatatctcct tcttaaagtt aaacaaaatt atttctagtg ggaaaccgtt gtg       53

<210> SEQ ID NO 19
<211> LENGTH: 7455
<212> TYPE: DNA
<213> ORGANISM: Artificial Sequence
<220> FEATURE:
<223> OTHER INFORMATION: Sequence of plastid expression construct
      pCGN6408
<220> FEATURE:
<221> NAME/KEY: misc_feature
<222> LOCATION: (1)...(2432)
<223> OTHER INFORMATION: trnV homologous recombination sequence
<220> FEATURE:
<221> NAME/KEY: terminator
<222> LOCATION: (2433)...(2734)
<223> OTHER INFORMATION: Trps16 transcription termination sequence
<220> FEATURE:
<221> NAME/KEY: misc_feature
<222> LOCATION: (2735)...(3532)
<223> OTHER INFORMATION: aadA sequence
<220> FEATURE:
<221> NAME/KEY: promoter
<222> LOCATION: (3533)...(3766)
<223> OTHER INFORMATION: Prrn/G10L promoter/RBS
<220> FEATURE:
<221> NAME/KEY: promoter
<222> LOCATION: (3805)...(4028)
<223> OTHER INFORMATION: psbA promoter
<220> FEATURE:
<221> NAME/KEY: misc_feature
<222> LOCATION: (4030)...(4748)
<223> OTHER INFORMATION: GFPuvm coding sequence
```

```
<220> FEATURE:
<221> NAME/KEY: terminator
<222> LOCATION: (4749)...(4959)
<223> OTHER INFORMATION: psbA terminator
<220> FEATURE:
<221> NAME/KEY: misc_feature
<222> LOCATION: (4960)...(7454)
<223> OTHER INFORMATION: rps12/7 homology sequence

<400> SEQUENCE: 19
ggtacccgag tgaatagaaa gttggatcta cattggatct cacctgaatc gccccatcta      60
tcctcctgag gagaagtttg gtttcaaacc ccggttcgaa caggaggagt acgccatgct     120
aatgtgcctt ggatgatcca catctcaggg tcaggcgctg atgagcacat tgaactatcc     180
atgtggctga gagccctcac agcccaggca caacgacgca attatcaggg gcgcgctcta     240
ccactgagct aatagcccgt cgtgcgggcc tcctgctggg ggcccgctat gccaagccaa     300
aagcgagaga acccccatcc ctctctttcc tttttacgcc ccctgccgc cacacgagag      360
ggacatgggg gcgtaaaagg ggatcctatc aacttgttcc gacctaggat aataagctca     420
tgggcttttgg gtttgaagct gtgtcaaacc taaatatccca agaagcatta gctctccctg     480
aaaaggaggt gatccagccg caccttccag tacggctacc ttgttacgac ttcactccag     540
tcactagccc tgccttcggc accccccctcc ttgcggttaa ggtaacgact tcggcatgg      600
ccagctccca tagtgtgacg ggcggtgtgt acaaggcccg ggaacgaatt caccgccgta     660
tggctgaccg gcgattacta gcgattccgg cttcatgcag gcgagttgca gcctgcaatc     720
cgaactgagg acgggttttt ggagttagct caccctcgcg ggatcgcgac cctttgtccc     780
ggccattgta gcacgtgtgt cgcccagggc ataaggggca tgatgacttg acgtcatcct     840
cacctttcctc cggcttatca ccggcagtct gttcagggtt ccaaactcaa cggtggcaac     900
taaacacgag ggttgcgctc gttgcgggac ttaacccaac accttacggc acgagctgac     960
gacagccatg caccacctgt gtccgcgttc ccgaaggcac ccctctcttt caagaggatt    1020
cgcggcatgt caagccctgg taaggttctt cgctttgcat cgaattaaac cacatgctcc    1080
accgcttgtg cgggccccccg tcaattcctt tgagtttcat tcttgcgaac gtactcccca    1140
ggcgggatac ttaacgcgtt agctacagca ctgcacgggt cgatacgcac agcgcctagt    1200
atccatcgtt tacggctagg actactgggg tatctaatcc cattgctcc cctagctttc     1260
gtctctcagt gtcagtgtcg gcccagcaga gtgctttcgc cgttggtgtt ctttccgatc    1320
tctacgcatt tcaccgctcc accggaaatt ccctctgccc ctaccgtact caagcttggt    1380
agtttccacc gcctgtccag ggttgagccc tgggatttga cggcggactt aaaaagccac    1440
ctacagacgc tttacgccca atcattccgg ataacgcttg catcctctgt attaccgcgg    1500
ctgctggcac agagttagcc gatgcttatt ccccagatac cgtcattgct tcttctctgg    1560
gaaaagaagt tcaggacccg taggccttct acctccacgc ggcattgctc cgtcaggctt    1620
tcgcccattg cggaaaattc cccactgctg cctcccgtag gagtctgggc cgtgtctcag    1680
tcccagtgtg gctgatcatc ctctcggacc agctactgat catcgccttg gtaagctatt    1740
gcctcaccaa ctagctaatc agacgcgagc ccctcctcgg gcggattcct ccttttgctc    1800
ctcagcctac gggtattag cagccgtttc cagctgttgt tccccctccca agggcaggtt    1860
cttacgcgtt actcacccgt ccgccactgg aaacaccact tcccgtccga cttgcatgtg    1920
ttaagcatgc cgccacgcgtt catcctgagc caggatcgaa ctctccatga gattcatagt    1980
tgcattactt atagcttcct tcttcgtaga caaagctgat tcggaattgt ctttcattcc    2040
```

-continued

```
aagtcataac ttgtatccat gcgcttcata ttcgcatgga gttcgctccc agaaatatag    2100
ctacccctac cccctcacgt caatcccacg agcctcttat ccattcttat tcgatcacag    2160
cgagggagca agtcaaaata gaaaaactca cattcattgg gtttagggat aatcaggctc    2220
gaactgatga cttccaccac gtcaaggtga cactctaccg ctgagttata tcccttcccc    2280
catcaagaaa tagaactgac taatcctaag tcaaagggtc gagaaactca aggccactat    2340
tcttgaacaa cttggattgg agccgggctt cctttcgca ctattacggg tatgaaatga     2400
aaataatgga aaaagttgga ttcaattgtc ggcgcgccat tttatatatt ttctatacaa    2460
taattctata caataaaatt ttgtatttat acaaaattta gaatttctat aaacccaaaa    2520
attttttaat aaatttgttt tttattataa aacatggtag ttttttagcag atatttgtt    2580 agttttcata cctttaggaa gaatactaat aataaatgga aattctaata aatcaaaata    2640
aatatgatgg aaacgaaaga ggaggaaaga aagagtaga tcaaatttga taccaagcta    2700
tatatgagtc tttaacatcc tcttttttat agttctagaa ttatttgccg actaccttag    2760
tgatctcgcc tttcacgtag tggacaaatt cttccaactg atctgcgcgc gaggccaagc    2820
gatcttcttc ttgtccaaga taagcctgtc tagcttcaag tatgacgggc tgatactggg    2880
ccggcaggcg ctccattgcc cagtcggcag cgacatcctt cggcgcgatt ttgccggtta    2940
ctgcgctgta ccaaatgcgg gacaacgtaa gcactacatt tcgctcatcg ccagcccagt    3000
cgggcggcga gttccatagc gttaaggttt catttagcgc ctcaaataga tcctgttcag    3060
gaaccggatc aaagagttcc tccgccgctg gacctaccaa ggcaacgcta tgttctcttg    3120
cttttgtcag caagatagcc agatcaatgt cgatcgtggc tggctcgaag atacctgcaa    3180
gaatgtcatt gcgctgccat tctccaaatt gcagttcgcg cttagctgga taacgccacg    3240
gaatgatgtc gtcgtgcaca acaatggtga cttctacagc gcggagaatc tcgctctctc    3300
caggggaagc cgaagtttcc aaaagtcgt tgatcaaagc tcgccgcgtt gtttcatcaa     3360
gccttacggt caccgtaacc agcaaatcaa tatcactgtg tggcttcagg ccgccatcca    3420
ctgcggagcc gtacaaatgt acggccagca acgtcggttc gagatggcgc tcgatgacgc    3480
caactacctc tgatagttga gtcgatactt cggcgatcac cgcttcccctt cccatgggta   3540 tatctccttc ttaaagttaa acaaaattat ttcagtgggg aaaccgttgt ggtctcccta    3600
caaagctgat tcggaattgt cttcattcc aagtcataac ttgtatccat gcgcttcata     3660
ttcgcatgga gttcgctccc agaaatatag ctaccccctac cccctcacgt caatcccacg   3720
agcctcttat ccattcttat tcgatcacag cgagggagca agtcggccgg ccttggatcc    3780
cccgggctgc aggaattcat ttaattaatt atatttctat gtatatagat tcgtttataa    3840
tttctctcct cgataaaaaa attattatga atctaaacta aaaggatctt agccatttta    3900
cattggttga catggctata taagtcatgt tatactgttc aataacaagc tctcaattat    3960
ctacttatag ttttagagaa tttgtgtgct tgggagtccc tgatgattaa ataaaccaag    4020
gattttacca tgggtaaagg agaagaactt ttcactggag ttgtcccaat tcttgttgaa    4080
ttagatggtg atgttaatgg gcacaaattt tctgtcagtg gagagggtga aggtgatgca    4140
acatacggaa aacttaccct taaatttatt tgcactactg gaaaactacc tgttccttgg    4200
ccaacacttg tcactactct tacttatggt gttcaatgct tttcccgtta tccggatcat    4260
atgaaacggc atgacttttt caagagtgcc atgcccgaag ttatgtaca ggaacgcact     4320 atatctttca aagatgacgg gaactacaag acgcgtgctg aagtcaagtt tgaaggtgat    4380
acccttgtta atcgtatcga gttaaaaggt attgatttta aagaagatgg aaacattctc    4440
```

```
ggacacaaac tcgagtacaa ctataactca cacaatgtat acatcrcggc agacaaacaa    4500
aagaatggaa tcaaagctaa cttcaaaacc cgccacaaca ttgaagatgg aggcgttcaa    4560
ctagcagacc attatcaaca aaatactcca attggcgatg cccctgtcct tttaccagac    4620
aaccattacc tgtcgacaca atctgccctt tcgaaagatc ccaacgaaaa gcgtgaccac    4680
atggtccttc ttgagtttgt aactgctgct gggattacac atggcatgga tgagctctaa    4740
aataatatct agattcttta gtgttagtct atacctagtt tagtaatatt aaaaacgagc    4800
gatataagcc ttattttaa ggcttatatc gctcgttttt ttctataaaa cggaacaaat    4860 cattttttt atataattt ttctattata tataaaatag aaaaaaatac tattataatt    4920 tataatttt ttttatcaa aaaaaatatt gctgcgtgcg gccgcaacta ctcctatcgg    4980
aaataggatg actacggatt cgagccatag cacatggttt cataaaaccg tacgattctc    5040
ccgatctaaa tcaagccggt tttacatgaa gaagatttta ctcagcatgt tctattcgat    5100
acgggtagga gaaacggtat tcttttctta aacttcgaaa aatagagaaa tcagaaccaa    5160
gtcaagatga tacggattaa ttcctttattc ttgcgccaaa gatcttccta tttccaaagg    5220
aactggagtt acatctcttt tccattttcca ttcaagagtt cttatgtgtt tccacgcccc    5280
tttaagaccc cgaaaaatta acaaattccc ttttcttagg aacacgtgcg agataaaaaa    5340
aaaaagagag aatggtaacc ccacgattaa ctatttcatt tatgaatttc atagtaatag    5400
aaatacatgt cctaccgaaa cagaatttgt aacttgctat cctataatct tgcctagcag    5460
gcaaagattt cactccgcga aaaagatgat tcattcggat caacatgaaa gcccaactac    5520
attgcattgc cagaattcat gttatctatt ggaaagaggt tgacctcctt gcttctatgg    5580
tacaatcctc ttcccgctga gcctcctttc ttccgtgatt aactgttggc accagtccta    5640
cattttgtct ctgtggaccg agaagaaagg actcactgcg ccaagatcac taactaacac    5700
taatctaata gaatagaaaa tcctaatata atagaaaaga actgtctttt ctgtatactt    5760
atgtatactt tcccccggttc cgttgctact gcgggcttta cgcaatcgat cggatcatct    5820
agatatccct tcaacacaac ataggtcgtc gaaaggatct cggagacccg ccaaagcacg    5880
aaagccagga tctttcagaa aataaattcc tattcgaaga gtgcataacc gcatggataa    5940
gctcacacta acccgtcaat ttgggatcca attcgggatt ttccttgagg gatattggta    6000
aggaattgga atgtaataat atcgattcat aatggattca tatcgataca gaagaaaagg    6060
ttctctatcg attcaacaag tgctgtactt atgggaaagc gatagagaaa gagaaaaaaa    6120
aaacgaagat ttcacatagt gatttttttt tgatcaaaaa aaatatgat tgaatttatt    6180 tcgtacccctt cgctcaatga gaacatgggt cagattctat aggatcaaac ctatgggact    6240
taagaatgat ggaagggaat aaaatcaaaa aagaaatcaa ataagaaaa gagagggaaa    6300 ataagaaaat aataagtaaa taaaaatgaa gtagaagaac ccagattaca aatgaacaaa    6360
ttcaaacttg aaaagtctc tttctgattc tcgaagaatg aggggcaaag agattgatcg    6420
agaaagatct cttgttctta ttataagatc gtgtgattgg accgcagat gtttggtaaa    6480 aagaataatc ttatcctttg agaataatca aaaatagaaa gtgttcaatt ggaacatgaa    6540
aacgtgaccg agtttatcct agttactctt cgggacggag gagattcgcg aacgaggaaa    6600
gggacccaat gacttcgaaa gaattgaacg aggagccgta tgaggtgaaa atctcatgtc    6660
cggttctgta gagtggcagt aagggtgact tatctgtcaa cttttccact atcaccccca    6720
aaaaaccaaa ctctgcctta cgtaaagttg ccagagtacg attaacctcg ggatttgaaa    6780
```

```
tcactgctta tatacctggt attggccata atttacaaga acattctgta gtcttagtaa   6840
gagggggaag ggttaaggat ttacccggtg tgagatatca cattgttcga ggaaccctag   6900
atgctgtcgg agtaaaggat cgtcaacaag ggcgttctag tgcgttgtag attcttatcc   6960
aagacttgta tcatttgatg atgccatgtg aatcgctaga aacatgtgaa gtgtatggct   7020
aacccaataa cgaaagtttc gtaagggac tgaagcaggc taccatgaga caaaagatct    7080
tctttcaaaa gagattcaat tcggaactct tatatgtcca aggttcaata ttgaaataat   7140
ttcagaggtt ttccctgact ttgtccgtgt caacaaacaa ttcgaaatgc ctcgactttt   7200
ttagaacagg tccgggtcaa atagcaatga ttcgaagcac ttatttttac actatttcgg   7260
aaacccaagg actcaatcgt atggatatgt aaaatacagg atttccaatc ctagcaggaa   7320
aaggagggaa acggatactc aatttaaaag tgagtaaaca gaattccata ctcgatttca   7380
tagatacata tagaattctg tggaaagccg tattcgatga aagtcgtatg tacggtttgg   7440
agggagatcg agctc                                                   7455
```

PLASTID TRANSFORMATION OF *BRASSICA*

Cross-Reference to Related Applications

This application is a divisional of application Ser. No. 09/465,856 filed 17 Dec. 1999, now Abandoned, which is a continuation of application Ser. No. 09/220,557 filed 23 Dec. 1998, now U.S. Pat. No. 6,515,206.

TECHNICAL FIELD

The invention relates to methods of genetically transforming plant plastids, and more specifically to genetically transforming the plastid genomes of *Brassica* plant species.

BACKGROUND

The plastids of higher plants are an attractive target for genetic engineering. Plant plastids (chloroplasts, amyloplasts, elaioplasts, etioplasts, chromoplasts, etc.) are the major biosynthetic centers that, in addition to photosynthesis, are responsible for production of industrially important compounds such as amino acids, complex carbohydrates, fatty acids, and pigments. Plastids are derived from a common precursor known as a proplastid and thus the plastids present in a given plant species all have the same genetic content. In general, plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest which potentially can result in very high levels of foreign gene expression. In addition, plastids of most plants are maternally inherited. Consequently, unlike heterologous genes expressed in the nucleus, heterologous genes expressed in plastids are not pollen disseminated, therefore, a trait introduced into a plant plastid will not be transmitted to wild-type relatives.

Plastids of higher plants present an attractive target for genetic engineering. As mentioned above, plastids of higher plants are maternally inherited. This offers an advantage for genetic engineering of plants for tolerance or resistance to natural or chemical conditions, such as herbicide tolerance, as these traits will not be transmitted to wild-type relatives. A review of plastid transformation of flowering plants is provided by Maliga (1993) *Trends in Biotech.* 11:101–107, the entirety of which is incorporated herein by reference.

Unfortunately, successful plastid transformation techniques described thusfar for higher plants have been limited to model crop plants such as tobacco (U.S. Pat. No. 5,451,513; Svab et.al. (1990), *Proc. Natl. Acad. Sci. USA* 87:8526–8530 and Svab et al. (1993), *Proc. Natl. Acad. Sci. USA* 90:913–197) and *Arabidopsis* (Sikdar, et al. (1998) *Plant Cell Reports* 18:20–24). Furthermore, the methods described for *Arabidopsis* plants, produce infertile regenerates. PCT Publication WO 97/32977 also describes methods for the plastid transformation of *Arabidopsis* and provides prophetic examples of plastid transformation of *Brassica* plastids. However, transplastomic *Brassica* plants have not been produced to date using the methods described therein. Thus, for practical applications of genetic engineering techniques to crop plant plastids, chloroplast transformation techniques for a wide variety of crop plants, such as *Brassica* species, are needed in the art.

Chloroplast transformation methods applicable to crop species, such as *Brassica* species, are needed in the art. Such methods would provide for a novel means of genetic engineering via plastid transformation for agronomically as well as qualitatively important traits via genetic engineering of plant plastids.

SUMMARY OF THE INVENTION

The present invention provides constructs and methods for the transformation and regeneration of *Brassica* plants containing plant cells, the plastids of which have been stably transformed by a foreign DNA of interest. The method generally comprises transforming a *Brassica* plant cell plastid with a DNA construct having regions of homology obtained from the *Brassica* plastid genome; selecting for cells which contain the DNA construct; and obtaining a mature multicellular plant, the cells of which contain the DNA construct in the plant cell plastid.

A first aspect of the present invention provides methods for transforming the plastids of *Brassica* plant cells with a DNA construct generally comprising, in the 5' to 3' direction of transcription, a promoter region functional in a plant cell plastid, a DNA sequence of interest, and a transcription termination region functional in a plant cell plastid. The constructs further comprise regions of homology derived from *Brassica* plastid sequences.

Another aspect of the present invention provides nucleic acid constructs having a promoter functional in a *Brassica* plant cell plastid, a nucleic acid sequence of interest, and a transcription termination sequence functional in a plant cell plastid. The constructs can also contain regions of homology for the integration of the construct into the host cell plastid genome. The regions of homology are preferably obtained from the *Brassica* plastid genome sequence.

In another aspect of the present invention, methods for expressing a nucleic acid sequence in a host *Brassica* plant cell plastid are provided. In general, the methods involve introducing into a host *Brassica* plant cell a recombinant nucleic acid construct having a promoter functional in a plastid, a nucleic acid sequence of interest, and a transcriptional termination sequence functional in a plant cell plastid.

In yet another aspect of the present invention, multicellular *Brassica* plant obtained by the methods described herein are provided.

The invention also provides a multicellular *Brassica* plant, the plastids of which have been transformed with a DNA construct of interest.

The invention also provides a method for obtaining a *Brassica* plant cell, of which the plastid has been stably transformed with a DNA construct, comprising in the 5' to 3' direction of transcription, a promoter functional in a plant cell plastid, a DNA sequence encoding a green fluorescent protein (herein referred to as GFP), and a transcriptional termination region functional in a plant cell plastid.

DETAILED DESCRIPTION OF THE INVENTION

Figure 1:
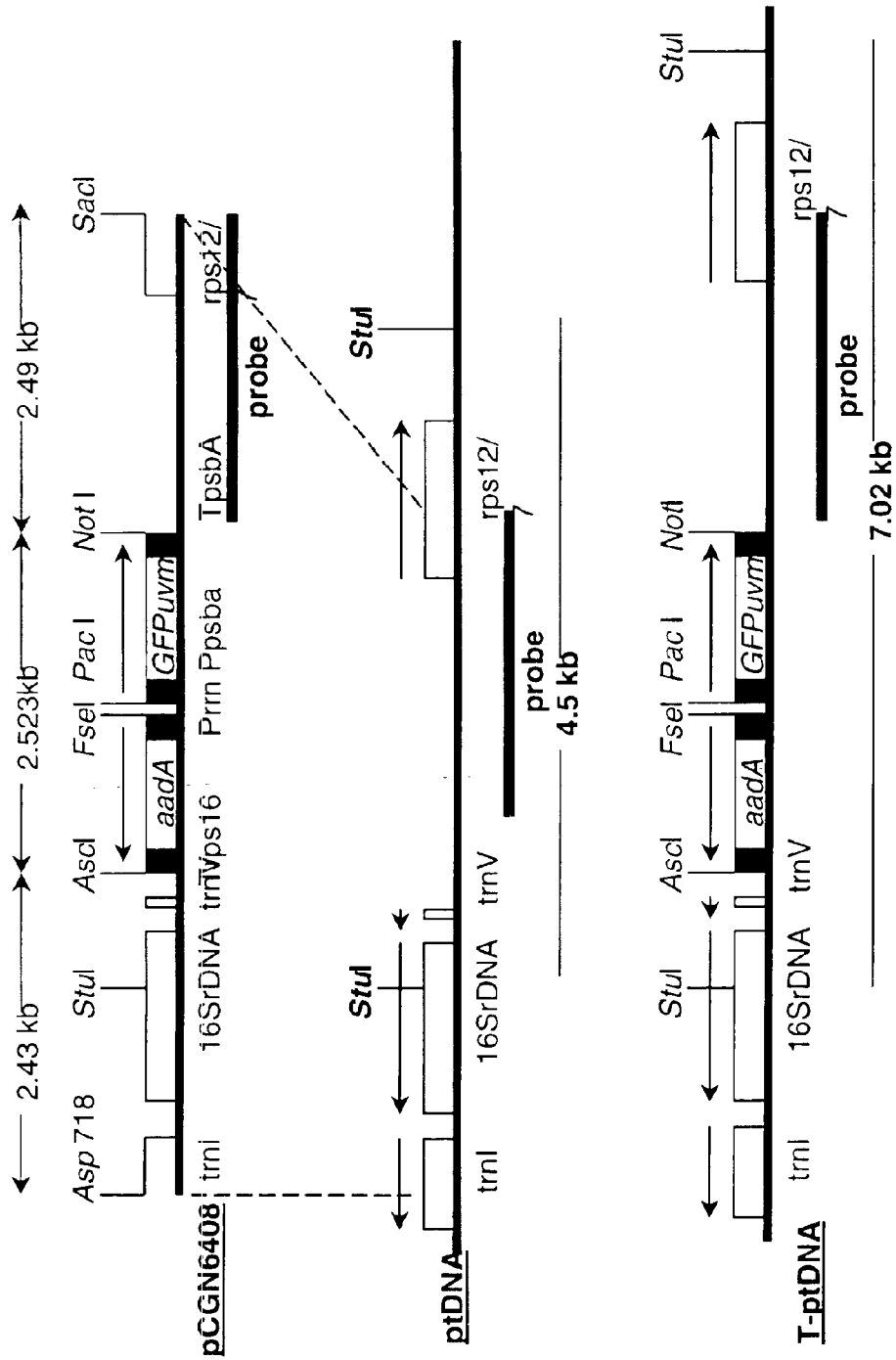
FIG. 1 provides a construct for preparation of transplastomic *Brassica* lines containing a GFP expression marker. A schematic of the pCGN6408 construct and representation of incorporation into the tobacco plastid genome are shown at the top. Lines above the aadA and GFP boxes indicate the direction of transcription. Expected sizes for StuI fragments are provided for the incoming DNA as well as the wild type DNA (ptDNA).

In accordance with the subject invention, constructs and methods are provided for obtaining *Brassica* plant cells containing plastids into which heterologous DNA has been inserted. The method generally encompasses transforming a *Brassica* plant cell with plastid expression vectors. The plastid expression constructs generally contain nucleic acid sequences comprising, as operably associated components in the 5' to 3' direction of transcription, a promoter region functional in a plant plastid, a DNA sequence of interest, and a transcription termination region capable of terminating transcription in a plant plastid. The constructs for use preferably comprise regions of homology for integration into the host plant cell plastid genome. The regions of homology are preferably obtained from *Brassica* genome sequence. The term "obtained" as used herein refers to any sequence analogous to a region of homology of a *Brassica* plastid genome sequence. Such sequence can be produced in accordance with any method known in the art and include but not limited to synthesis, amplification from a plastid genomic sequence, or cloned from *Brassica* plastid genomic sequences.

In one aspect of the present invention a method of producing a plant cell from a *Brassica* plant species wherein the plastids of the plant contain a recombinant nucleic acid construct to direct the expression of a nucleic acid sequence of interest from the plant cell plastid.

The methods generally comprise introducing recombinant nucleic acid constructs into plant cell plastids in prepared tissue sources from *Brassica* plant species. The nucleic acid constructs can be integrated into the plastid genome, or can be contained as self-replicating plasmids within the plastid. Preferably, the constructs are integrated into the plant cell plastid genome using homologous recombination sequences obtained from a *Brassica* plastid genome.

The plant cell used in the methods of the present invention can be obtained from any plant tissue source which contain plastids, and which has the ability to regenerate into a mature plant or structure which will give rise to a mature plant. Such tissues include, but are not limited to, leaf tissue, cotyledons (including cotyledonary notch), hypocotyls, epicotyls, stem sections, embryogenic callus, callus, petioles, protoplasts, stem thin layers, microspores, as well as some seeds and embryos. Preferably, the cells used in the methods of the present invention are obtained from leaf tissue. Furthermore, the tissue source can be derived from plants grown in a variety of conditions, including in vitro, soil grown, and the like.

Prior to transformation, the tissue source can be treated with various osmotic pressures. Osmotic treatment refers to culturing the tissue on a medium containing sugar alcohols, including but not limited to sorbitol and mannitol. The osmotic treatment can also be performed after transformation, during transformation, or before, during and after transformation. Concentrations of sugar alcohols for use in the treatments include ranges from about 0.01M to about 1.0M, preferably from about 0.05M to about 0.7M, more preferably from about 0.1M to about 0.5M, most preferably from about 0.2M to about 0.4M.

Constructs for transformation into a *Brassica* plant cell can be introduced using any available method. Methods for introduction include, but are not limited to, biolistic transformation, PEG mediated transformation, and electroporation. Preferably, DNA constructs of interest are transformed into the plastids of a plant cell from a desirable host tissue using particle gun bombardment. General methods for biolistic transformations are described by Sanford, et al. (1993) *Methods in Enzymology* 217:483–509, and Ye, et al. (1990) *Plant Molecular Biology* 15:809–819. Stable transformation of tobacco plastid genomes by particle bombardment is reported (Svab et.al. (1990 supra) and Svab et al. (1993 supra)). The methods reported therein, can be employed in the transformation methods of the present invention. Other methods are known in the art, and are described by O'Neil, et al. (1993) *Plant Journal* 3:729–738 and Golds, et al. (1993) *Bio/Technology* 11:95–97.

The regeneration of whole plants from a transformed cell contained in the transformed tissue used in transformation involves several growth stages. Typically, a tissue, having been excised from an adult plant or germinated seedling, is placed in a chemically defined medium under sterile conditions. By growing the explant under such controlled conditions for a period of time, an undifferentiated mass of cells, referred to as a callus, can form.

By culturing this callus under the proper set of conditions, e.g., nutrients, light, temperature, humidity, and by providing the proper combination and concentration of plant growth regulators, the calli can be induced to form differentiated cells and regenerate plant shoots. Plant shoots, sometimes referred to as plantlets, containing meristem tissue are then transferred to a media for the induction of root production.

Preferably, tissue into which a plastid construct has been introduced is cultured on a cell division, or cell expansion, promoting media, referred to as delay medium. The delay medium can be either liquid or solid, or semi-solid by the addition of a solidifying agent, such as agar. The tissue is preferably cultured on delay medium for a period ranging from about 0 days to about 14 days, preferably from about 1 day to about 10 days, more preferably from about 1 day to about 7 days, most preferably from about 2 days to about 7 days, after which the plant tissue is transferred to a selective media containing an inhibitory amount of the particular selective agent, as well as the particular hormones and other substances necessary to obtain regeneration for that particular plant species. Shoots are then subcultured on the same selective media, containing higher, lower or the same concentration of the particular selective agent, to ensure production and selection of homoplasmic shoots.

The selective media can be liquid or solid or semi-solid by the addition of a solidifying agent, such as agar. Liquid selective media allows for greater surface area of contact of the plant tissue with the selective media containing particular hormones, particular selective agent and other substances necessary to obtain regeneration.

The amount of selective agent can remain constant in the media during regeneration. Alternatively, the amount of selective agent can initially be at higher levels, then lowered during later stages of regeneration. Furthermore, the selective agent amount can be lower during the initial stages of regeneration, then increased later in regeneration.

Transplastomic plants are analyzed for a pure population of transformed plastid genomes (homoplasmic lines). Homoplasmy can be verified using Southern analysis employing nucleic acid probes spanning a region of the transgene and chloroplast genome (i.e. the insertion region). Transplastomic plants which are heteroplasmic (i.e. contain a mixture of plastid genomes containing and lacking the transgene) are characterized by a hybridization pattern of wild type and transgenic bands. Homoplasmic plants show a hybridization pattern lacking the wild type band.

Alternatively, homoplasmy can be verified using the polymerase chain reaction (PCR). PCR primers are utilized which are targeted to amplify from sequences from the insertion region. For example, a pair of primers can be utilized in a PCR reaction. One primer amplifies from a region in the transgene, while the second primer amplifies from a region proximal to the insertion region towards the insertion region. A second PCR reaction is performed using primers designed to amplify the region of insertion. Transplastomic lines identified as homoplasmic produce the expected size fragment in the first reaction, while they do not produce the predicted size fragment in the second reaction.

As described in more detail in the examples below, transplastomic *Brassica* plants are produced from methods described herein.

Other *Brassica* plant species can be similarly transformed using the methods of the present invention. Suitable plants for the practice of the present invention include, but are not limited to, diploid *Brassica* species including *B. rapa, B. oleracea,* and *B. nigra,* as well as amphidiploid species including *B. napus, B. juncea,* and *B. carinata.* The methods of the present invention can also find use in the transformation of plastids of closely related plants such as *Arabidopsis.*

Another aspect of the present invention provides recombinant nucleic acid constructs having a promoter functional in a plant cell plastid, a nucleic acid sequence of interest, and a transcriptional termination region functional in a plant cell plastid.

As used herein, a "recombinant nucleic acid construct" is a nucleic acid construct, generated recombinantly or synthetically, with a series of specified nucleic acid elements which permit transcription of a particular nucleic acid in a target cell. The recombinant nucleic acid construct includes an expression cassette which can be incorporated into a plasmid, chromosome, mitochondrial DNA, plastid DNA, virus, or nucleic acid fragment. Typically, the recombinant expression cassette portion of a nucleic acid construct includes, among other sequences, a nucleic acid sequence to be transcribed and a promoter.

A number of promoters are available to the skilled artisan which are functional in plant cell plastids. Such promoters include, but are not limited to, those derived from promoter regions of highly expressed plastid genes such as the promoter regions from the 16S ribosomal RNA operon (Prrn), psbA gene (PpsbA) or the rbcL gene (PrbcL). Additional elements can also be employed with the promoter regions to enhance transcription, translation, or both. Such elements include, but are not limited to, ribosome binding sites, Shine-Delgarno sequences, enhancer elements, and the like.

The nucleic acid sequence for use in the recombinant construct can be any nucleic acid sequence of interest for transcription or transcription and translation (expression) in a host plant cell plastid. Sequences of interest include but are not limited to sequences encoding for genes involved in tolerance to herbicides, reporter genes, selectable markers, mammalian proteins, and pathogen resistance.

Nucleic acid sequences encoding for proteins involved in herbicide tolerance are known in the art, and include, but are not limited to DNA sequences encoding for 5-enolpyruvylshikimate-3-phosphate synthase (EPSPS, described in U.S. Pat. Nos. 5,627,061, and 5,633,435, Padgette et al. (1996) *Herbicide Resistant Crops*, Lewis Publishers, 53–85, and in Penaloza-Vazquez, et al. (1995) *Plant Cell Reports* 14:482–487) and aroA (U.S. Pat. No. 5,094,945) for glyphosate tolerance, bromoxynil nitrilase (Bxn) for Bromoxynil tolerance (U.S. Pat. No. 4,810,648), phytoene desaturase (crtI (Misawa et al, (1993) *Plant Journal* 4:833–840, and (1994) *Plant Jour* 6:481–489) for tolerance to norflurazon, acetohydroxyacid synthase (AHAS (Sathasiivan et al. (1990) *Nucl. Acids Res.* 18:2188–2193)) and the bar gene for tolerance to glufosinate (DeBlock, et al. (1987) *EMBO J.* 6:2513–2519.

It should be noted that the expression constructs of the present invention can also include sequences encoding genes involved in other stress tolerances, for example insect or disease resistance/tolerance genes. Such insect tolerance genes are known in the art, for example the *Bacillus thurigiensis* cryl Ac protein.

In addition, the expression constructs also find use in directing the production of human biological proteins (pharmaceutical proteins) from the plant plastid. Nucleic acid sequences encoding for the Human Growth Hormone (hGH) can be employed in the plastid expression constructs of the present invention.

Other sequences of interest for use in the expression constructs of the present invention for the production of human biological proteins is the production of aprotinin.

Other sequences which find use in the production of human biologics include sequences encoding for insulin or insulin precursors. The skilled artisan will recognize that many nucleotide sequences encoding for human biologics can be employed in the constructs of the present invention to direct their expression from a plant plastid such as those described in Goodman and Gelman (1990) *Pharmacological Basis of Therapeutics*, Pergaman Press, 8th Edition, Sections 14 and 15.

A number of reporter genes are available to the skilled artisan, and include but are not limited to GUS and green fluorescent protein (GFP). Analysis techniques for the expression of GUS from transgenic tissues involves destruction of tissues prior to staining. Generally, the tissue is infiltrated with a glucoronide containing solution, then destained with an alcohol solution to remove chlorophyll background. The stained tissue is then visually observed for GUS staining, as evidenced by a blue coloration of the cells expressing b-glucoronidase. Other reporter genes are also known in the art, for example the Green Fluorescent Protein (GFP) can be employed using non-destructive analysis methods. A general review of GFP is provided by Tsien (1998) *Annu. Rev. Biochem.* 67:509–544, the entirety of which is incorporated herein by reference.

As discussed in more detail in the examples that follow, constructs employing GFP are used to transform *Brassica* plants such that the transformed *Brassica* plant has integrated into the chloroplast genome the construct to direct the expression of the GFP from the plastid. Cells of plants expressing GFP can be visualized under ultraviolet (uv) light, without the need for destructive methods. Visualized under uv light, the cells expressing GFP fluoresce as a green color. Mutations in the GFP coding sequence shift the excitation wavelength to blue light, allowing for a more convenient visualization of expression on a green plant surface.

Furthermore, transplastomic *Brassica* plants are identified which are heteroplasmic for the DNA sequences of interest encoding the GFP gene. Transplastomic *Brassica* plants are obtained using the methods of the present invention to transform a DNA construct comprising a marker gene, such as GFP, expressed from a promoter sequence which is functional in a plant cell plastid. The transplastomic plant obtained herein demonstrate GFP expression as determined by visualization under uv microscopy.

In developing the constructs the various fragments comprising the regulatory regions and open reading frame can be subjected to different processing conditions, such as ligation, restriction enzyme digestion, PCR, in vitro mutagenesis, linkers and adapters addition, and the like. Thus, nucleotide transitions, transversions, insertions, deletions, or the like, can be performed on the DNA which is employed in the regulatory regions or the DNA sequences of interest for expression in the plastids. Methods for restriction digests, Klenow blunt end treatments, ligations, and the like are well known to those in the art and are described, for example, by Maniatis et al. (in *Molecular cloning: a laboratory manual* (1989) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation of the DNA by joining or removing sequences, linkers, or the like. Preferably, the vectors will be capable of replication to at least a relatively high copy number in *E. coli*. A number of vectors are readily available for cloning, including such vectors as pBR322, vectors of the pUC series, the M13 series vectors, and pBluescript vectors (Stratagene; La Jolla, Calif.).

In order to provide a means of selecting the desired plant cells, vectors for plastid transformation typically contain a construct which provides for expression of a selectable marker gene. Marker genes are plant-expressible DNA sequences which express a polypeptide which resists a natural inhibition by, attenuates, or inactivates a selective substance, i.e., antibiotic, herbicide etc.

Alternatively, a marker gene can provide some other visibly reactive response, i.e., can cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct.

Detection of the marker phenotype makes possible the selection of cells having a second gene to which the marker gene has been linked. This second gene typically comprises a desirable phenotype which is not readily identifiable in transformed cells, but which is present when the plant cell or derivative thereof is grown to maturity, even under conditions wherein the selectable marker phenotype itself is not apparent.

The use of such a marker for identification of plant cells containing a plastid construct has been described by Svab et al. (1993, supra). In the examples provided below, a bacterial aadA gene is expressed as the marker under the regulatory control of chloroplast 5' promoter and 3' transcription termination regions, specifically the regulatory regions of the psbA gene (described in Staub et al., *EMBO J.*(1993) 12(2):601–606). Numerous additional promoter regions can also be used to drive expression of the selectable marker gene, including various plastid promoters and bacterial promoters which have been shown to function in plant plastids.

Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Cells which do not contain the selectable marker gene product are bleached or purple in color. Selection for the aadA gene marker is thus based on identification of plant cells which are not bleached by the presence of streptomycin, or more preferably spectinomycin, in the plant growth medium.

A number of markers have been developed for use with plant cells, such as resistance to chloramphenicol, the aminoglycoside G418, hygromycin, or the like. Other genes which encode a product involved in chloroplast metabolism can also be used as selectable markers. For example, genes which provide resistance to plant herbicides such as glyphosate, bromoxynil or imidazolinone can find particular use. Such genes have been reported (Stalker et al., *J. Biol. Chem.* (1985) 260:4724–4728 (glyphosate resistant EPSP); Stalker et al., *J. Biol. Chem.* (1985) 263:6310–6314 (bromoxynil resistant nitrilase gene); and Sathasivan et al., *Nucl. Acids Res.* (1990) 18:2188 (AHAS imidazolinone resistance gene)).

The vectors for use in plastid transformation can include sequences to provide for an origin of replication to allow the introduced construct to replicate autonomously in the plastid. Such sequences are known in the art and are described in U.S. Pat. No. 5,693,507, the entirety of which is incorporated herein by reference.

The vectors for use in plastid transformation preferably include means for providing a stable transfer of the plastid expression construct and selectable marker construct into the plastid genome. This is most conveniently provided by regions of homology to the target plastid genome. The regions of homology flank the expression construct to be transferred and provide for transfer to the plastid genome by homologous recombination, via a double crossover into the genome. The complete DNA sequence of the plastid genome of tobacco has been reported (Shinozaki et al., *EMBO J.* (1986) 5:2043–2049). Complete DNA sequences of the plastid genomes from liverwort (Ohyama et al., *Nature* (1986) 322:572–574) and rice (Hiratsuka et al., *Mol. Gen. Genet.* (1989) 217:185–194), have also been reported.

Where the regions of homology are present in the inverted repeat regions of the plastid genome (known as IRA and IRB), two copies of the transgene are expected per transformed plastid. Where the regions of homology are present outside the inverted repeat regions of the plastid genome, one copy of the transgene is expected per transformed plastid. The regions of homology within the plastid genome are approximately 1 kb to 3 kb in size. Smaller regions of homology can also be used, and as little as 100 bp can provide for homologous recombination into the plastid genome. However, the frequency of recombination and thus the frequency of obtaining plants having transformed plastids decreases with decreasing size of the homology regions.

Examples of constructs having regions of homology the tobacco plastid genome are described in Svab et al. (1990 supra), Svab et al. (1993 supra) and Zoubenko et al. (*Nuc Acid Res* (1994) 22(19):3819–3824). Examples of constructs having regions of homology to the *Arabidopsis* plastid genome are described by Sikdar, et al. (1998) supra.

As described herein, constructs are prepared using regions of homology derived from the sequences of the *Brassica* plastid genome to direct the homologous recombination of the heterologous DNA into the inverted repeat region of the plastid genome. Such regions of homology are obtained by utilizing PCR reactions to isolate sequences corresponding to the regions of homology in *Brassica* (also referred to herein as a homologous plastid genome). Thus, as used herein, regions of homology to a homologous plastid genome refers to DNA sequences which are used in the preparation of constructs to direct the integration of the expression construct into the plastid genome of the same plant genus as that from which the regions are derived.

The skilled artisan will recognize that additional regions of homology can also be utilized in accordance with the methods of the present invention. For example, regions of homology derived from other plant species plastid genomes can also be employed, for example, from *Arabidopsis*, or tobacco. Also, the regions of homology can also provide for homologous recombination in the plastid genome corresponding to the large single copy region:

Furthermore, the expression constructs provided herein utilize regulatory elements derived from the *Brassica* plastid genome. For example the promoter region obtained from *Brassica* 16S ribosomal RNA (Prrn) is used for the expression of the selectable marker aadA. Other regulatory regions derived from the *Brassica* plastid genome are also used in the constructs of the present invention, such as the terminator sequence of rps 16 as well as both the promoter and transcription termination regions of psbA. The skilled artisan will recognize that regulatory elements derived from heterologous plastid genomes, such as Tobacco or *Arabidopsis* can also be used in the constructs of the present invention.

Also contemplated in the present invention is the introduction of two or more constructs into a single *Brassica* plant cell plastid. Such methods include, but are not limited to retransformation, co-transformation, and the like. Methods for co-transformation of plastids have been described for tobacco by Carrer, et al. (1995) *Bio/technology*, 13:791–794. Such methods allow for selection on one selective agent, followed by selection on a second selective agent. For example, one construct could contain an aadA expression cassette for selection on spectinomycin/streptomycin, and a second construct could contain a CP4 EPSPS expression cassette for selection on glyphosate.

Thus, expression constructs for use in the methods of the present invention find use in directing the expression of DNA sequences encoding genes involved in a wide variety of plant genetic engineering applications. Such genes can encode for proteins involved in agronomic traits (input traits) such as herbicide tolerance and disease resistance, or quality traits (output traits) such as fatty acid composition modification and carotenoid production. Furthermore, DNA sequences encoding for proteins for the production of human biologics in a plant cell plastid also find use in the expression constructs of the present invention.

Constructs can also be prepared as to regulate the transcription and/or transcription and translation (expression) of a DNA sequence of interest from the plant cell plastid. Such constructs are known in the art and are described in U.S. Pat. No. 5,576,198, the entirety of which is incorporated herein by reference. Such constructs can be used to direct the expression from cells of selected tissues in the host plant. For example, to direct the transcription and/or transcription and translation (expression) of a DNA sequence of interest from a plastid in a seed cell of a *Brassica* plant, promoters providing for enhanced expression in a seed are employed to direct the expression of T7 RNA polymerase from the plant cell nucleus.

Methods for the nuclear transformation of *Brassica* plants are known in the art, and are described for example in, Radke et al. (*Theor. Appl. Genet.* (1988) 75:685–694 and *Plant Cell Reports* (1992) 11:499–505).

Such methods can be used, for example, to modify the carotenoid biosynthetic pathway preferentially in seed plastids. Modification of carotenoid biosynthesis in seed is described for example in PCT Publication WO 98/06862, the entirety of which is incorporated herein by reference.

The invention now being generally described, it will be more readily understood by reference to the following examples which are included for purposes of illustration only and are not intended to limit the present invention.

EXAMPLES

Example 1

Construction of Vectors

Constructs and methods for use in transforming the plastids of higher plants are described in Zoubenko et al. (*Nuc Acid Res* (1994) 22(19):3819–3824), Svab et al. (*Proc. Natl. Acad. Sci.*(1990) 87:8526–8530 and *Proc. Natl. Acad. Sci.* (1993) 90:913–917), Staub et al. (*EMBO J.* (1993) 12:601–606) and in U.S. Pat. No. 5,576,198. The complete DNA sequences of the plastid genome of tobacco are reported by Shinozaki et al. (*EMBO J.* (1986) 5:2043–2049). The T7 bacteriophage gene 10 leader (G10L) is constructed by ligating two oligonucleotides the potential stem-loop structure as well as the Shine-Delgarno sequence. The oligonucleotides used are 5'-AGGGA GACCACAACG-GTTTCCCTCTAGAAATAATTTTGTTTAAC TTTAAGAAGGAGATATACC-3' (SEQ ID NO:1) and 5'-GGTATATCTCCTTCTTAAAGTTAAACAAAATTATTT CTAGAGGGAAACCGTTGTGGT CTCCCT-3' (SEQ ID NO:2).

A vector, pMON30125 was previously prepared to direct the integration and expression of a second mutated GFP (GFP-2)reporter gene and the aadA selectable marker gene from the plant plastid.

The GFP-2 was derived from the GFP-1 by two additional mutations (F64L and S65T, Cormack, et al., (1996) *Gene* 173:33–38). Such mutations shift the excitation wavelength to blue light. The GFP-2 gene, also referred to herein as GFPuvm, was cloned between the Prrn/rbcL promoter/ribosome binding site and Trps16 transcription termination sequence. The Prrn/rbcL sequence is as described in Svab et al. (1993, supra). The Trpsl6 fragment comprises the rpsl 6 gene 3'-regulatory region from nucleotides 5,087 to 4,939 in the tobacco plasmid DNA.

The expression cassette pMON30125 contains a marker gene, aadA, for selection on spectinomycin and streptomycin, and rps 7/12 for the integration, by homologous recombination, of the passenger DNA into trnV-rps7/12 intergenic region. The aadA marker gene is expressed from the psbA promoter and transcriptional termination sequences. The promoter region of the plastid psbA promoter (PpsbA) and terminator sequences (TpsbA) are described in Staub et al. (1993, *EMBO J.*, 12, 601–606).

In tobacco, homologous targeting of transgenes in the plastid genome between the trnV and rps12/7 has yielded stable transformants at a high efficiency (Zoubenko et al. (1994) supra). Although the plastid genome of *Brassica* is collinear with that of tobacco, sequencing of this target region revealed several stretches of marked differences. Therefore, a *Brassica*-specific plastid transformation vector, pCGN6408, is constructed using approximately 5.0 kb of target sequences derived from *Brassica*. PCGN6408 contains two transgene expression cassettes: 1) a selectable aadA gene conferring spectinomycin/streptomycin resistance and expressed using *Brassica* 16Srrn promoter region, bacterial T7 gene 10 leader containing ribosome binding site which has been found to function efficiently in plastids (described in co-pending U.S. patent application Ser. No. 09/113,690) and *Brassica* rps16 terminator sequences—Prrn-g10L:aadA:Trps16. 2) a green fluorescent protein (GFPuvm) marker gene expressed using *Brassica* psbA promoter and terminator sequences—PpsbA:GFPuvm:TpsbA. The two transgene expression cassettes are flanked by approximately 2.5 kb plastid targeting sequences in pCGN6408.

The vector pCGN6408 is constructed by cloning the GFPuvm and aadA gene cassettes as an AscI-NotI fragment from pCGN6399 into pCGN6407. pCGN6407 contains approximately 5.0 kb of plastid targeting sequences and is constructed by cloning approximately 2.5 kb flank sequence containing the rps12/7 region as a NotI-SacI fragment followed by cloning of trnV containing approximately 2.5 kb flank sequence as an Asp718-XhoI fragment into pBluescript II KS (+) (Stratagene). The approximately 2.5 kb flanks are PCR-amplified using *Brassica* total DNA, with primers (Table 1) SC175 and SC176 for Asp718-XhoI fragment and SC177 and SC178 for NotI-SacI fragment. pCGN6399 is constructed by cloning the EcoRI-HindIII fragment containing the chimeric GFPuvm gene casette into pCGN6398, which contains the aadA expression cassette. The chimeric green fluorescent protein (GFPuvm) gene cassette, PpsbA:GFPuvm:TpsbA, has promoter and terminator sequences derived from *Brassica* psbA. It is constructed by cloning the GFPuvm expression cassette from pMON30125 into the EcoRI and HindIII sites of pUC118 and replacing the regulatory regions with the PpsbA as EcoRI-NcoI fragment and TpsbA as SacI-HindIII fragment producing plasmid pCGN6388. The PpsbA is generated by PCR with primers SC186 and SC187 containing the appropriate restriction sites. Similarly, the TpsbA is PCR-amplified with primers SC188 and SC189 containing the appropriate restriction sites. The chimeric aadA gene has the rrn promoter (Prrn) fused with the gene-10 leader (g10L) from bacterial T7 phage and the terminator of rps16 (Trps16). The Trps16 is PCR-amplified primers SC193 and SC194 containing appropriate restriction sites, digested with SacI and XbaI and cloned into pBluescriptII SK (+) (Stratagene) to generate pCGN6387. Prrn is serially PCR-amplified with primer pairs SC190 and SC191, SC190 and SC203, and SC190 and SC192 to generate a Prrn-g10L fusion. The aadA gene is PCR-amplified from pMON30125 with primers SC198 and SC199 . The Prn-g10L is fused to aadA using overlapping primers SC198 and SC192, and the resulting Prrn-g10L:aadA fragment is amplified with primers SC190 and SC199. The Prrn-g10L:aadA fragment is digested with BamHI and XbaI and cloned into pCGN6387. The resulting plasmid containing Prrn-g10L:aadA:Trps16 is designated pCGN6398.

Sequences for the flanking regions as well as regulatory sequences for the marker and reporter genes are obtained from *Brassica napus* by PCR amplification with primers designed after known sequences of the same regions from other species. Conditions for the PCR reactions for amplifying the homology regions is as follows: 94° C. for 4 min; 30 cycles of 94° C. for 30 s, 50° C. for 30 s, 72° C. for 1 min 45 s; with a final extension at 72° C. for 7 min and for the regulatory regions: 94y ° C. for 4 min; 30 cycles of 94° C. for 15 s, 55° C. for 30 s, with a final extension for 7 min. Primer sequences are listed in Table 1.

TABLE 1

Primer Sequences

| NAME | SEQUENCE 5'—3' | SEQ ID |
|---|---|---|
| SC175 | ACTGGGTACCCGAGTGAATAGAAAGTTGGATCTACATTG | SEQ ID NO:3 |
| SC176 | ACTGCTCGAGGCGCGCCGACAATTGAATCCAACTTTTTCCATTATTT | SEQ ID NO:4 |
| SC177 | ACTGGCGGCCGCAACTACTCCTATCGGAAATAGGATTGACTA | SEQ ID NO:5 |
| SC178 | CATGGAGCTCGATCTCCCTCCAAACCGTACATACGACT | SEQ ID NO:6 |
| SC186 | GATCGAATTCATTTAATTAATTATATTTCTATGTATATAGATTCGTTTATAA | SEQ ID NO:7 |
| SC187 | GATCCCATGGTAAAATCCTTGGTTTATTTAATCATC | SEQ ID NO:8 |
| SC188 | GATCGAGCTCTACAAATAATGATCTAGATTCTTTAGTGTTAGTCTATACCTAGT | SEQ ID NO:9 |
| SC189 | GATCAAGCTTAGGCGGCCGCACGCAGCAATATTTTTTTTGATAA | SEQ ID NO:10 |
| SC190 | GATCGGATCCAAGGCCGGCCGACTTGCTCCCTCGCTGTGATCGAATAAG | SEQ ID NO:11 |
| SC191 | TTTCTAGTGGGAAACCGTTGTGGTCTCCCTACAAAGCTGATTCGGAATTGTCTTTC | SEQ ID NO:12 |
| SC192 | CGATACTTCGGCGATCACCGCTTCCCTTCCCATGGGTATATCTCCTTCTTAAAGTT | SEQ ID NO:13 |
| SC193 | GATCTTCTAGAACTATAAAAAAGAGGATGTTAAAGACTCATATATAGCTTG | SEQ ID NO:14 |
| SC194 | GATCGAGCTCATGGCGCGCCATTTTATATATTTTCTATACAATAATTCTATAC | SEQ ID NO:15 |
| SC198 | AGAAGGAGATATACCCATGGGAAGGGAAGCGGTGATCGC | SEQ ID NO:16 |
| SC199 | ACGTTCTAGAATTATTTGCCGACTACCTTAGTGATCTCG | SEQ ID NO:17 |
| SC203 | TATATCTCCTTCTTAAAGTTAAACAAAATTATTTCTAGTGGGAAACCGTTGTG | SEQ ID NO:18 |

A transformation vector is prepared to direct the integration and expression of a reporter and marker genes from the plant plastid using the flanking regions and the regulatory regions obtained above.

The vector pCGN6408 was constructed by cloning the GFPuvm and aadA gene cassettes as an AscI-NotI fragment from pCGN6399 (described below) into pCGN6407 (described below). The plasmid pCGN6407 contains approximately 5.0 kb of *Brassica* plastid targeting sequences and was constructed by cloning approximately 2.5 kb flanking sequence containing the rps12/7 region as a NotI-SacI fragment followed by cloning of trnV containing approximately 2.5 kb flank sequence as an Asp718-XhoI fragment into pblue script II KS (+) (Stratagene). The approximately 2.5 kb flanks were PCR-amplified using *Brassica* total DNA, with primers SC175 and SC176 for Asp718-XhoI fragment and SC177 and SC178 for NotI-SacI fragment. pCGN6399 was constructed by cloning the EcoRI-HindIII fragment containing the chimeric GFPuvm gene casette into pCGN6398, which contains the aadA expression cassette. The chimeric green fluorescent protein (GFPuvm) gene cassette, PpsbA:GFPuvm:TpsbA, has promoter and terminator sequences derived from *Brassica* psbA. It was constructed by cloning the GFPuvm expression cassette from pMON30125 into the EcoRI and HindIII sites of pUC118 and replacing the regulatory regions with the PpsbA as EcoRI-NcoI fragment and TpsbA as SacI-HindIII fragment producing plasmid pCGN6388. The PpsbA was generated by PCR with primers SC186 and SC187 containing the appropriate restriction sites. Similarly, the TpsbA was PCR-amplified with primers SC188 and SC189 containing the appropriate restriction sites. The chimeric aadA gene has the rrn promoter (Prrn) fused with the gene-10 leader (g10L) from bacterial T7 phage and the terminator of rps16 (Trps16 ). The Trps16 was PCR-amplified primers SC193 and SC194 containing appropriate restriction sites, digested with SacI and XbaI and cloned into pBluescriptII SK (+) (Stratagene) to generate pCGN6387. Prrn was serially PCR-amplified with primer pairs SC190 and SC191, SC190 and SC203, and SC190 and SC192 to generate a Prrn-g10L fusion. The aadA gene was PCR-amplified from pMON30125 with primers SC198 and SC199 . The Prrn-g10L was fused to aadA using overlapping primers SC192 and SC198 and the Prrn-g10L:aadA fragment amplified by primers SC190 and SC199. The Prrn-g10L:aadA fragment was then digested with BamHI and XbaI and cloned into pCGN6387. The resulting plasmid containing Prrn-g10L:aadA:Trps16 was designated pCGN6398.

The nucleic acid sequence of the *Brassica* plastid expression cassette is determined to confirm the sequences of the homology regions and the regulatory sequences, and is provided in SEQ ID NO: 19.

Example 2

Chloroplast Transformation

A. Establishment of Source Plants

Seeds of *Brassica napus* variety 212/86 are surface sterilized by immersion in 95% ethanol for 2 minutes, followed by 30 minutes in 20% Clorox with 1 drop of dish soap per 100 ml as a surfactant. The seeds are rinsed four times in sterile distilled water.

The sterilized seeds are sown in Magenta boxes (Magenta Corp. Chicago, Ill.) containing *Brassica* germination medium (Table 2). The boxes are placed in a growth room at 21° C. with a 16 hr light period and a light intensity of 55 photons/meter$^2$/second. Cotyledons are removed from two week old plants and the upper part of the shoots are excised from the roots and placed on *Brassica* in vitro plant medium (Table 3), one plant per box. Plants are grown under the same conditions as seedlings and are subcultured using the in vitro medium every four weeks.

TABLE 2

Germination Medium

| Component | Concentration |
|---|---|
| Murashige Minimal Organics | 3.457 g/L |
| Pyridoxine-HCL | 0.05 mg/L |
| Nicotinic Acid | 0.05 mg/L |
| Glycine | 0.2 mg/L |
| Phytagar | 6 g/L |
| pH adjusted to 5.8 | |

TABLE 3

In Vitro Plant (IVP) Medium

| Component | Concentration |
|---|---|
| 10x B5 Salts (Table 4) | 1x |
| 100x B5 Vitamins + inositol (Table 5) | 1x |
| Sucrose | 30 g/L |
| Phytagar | 6 g/L |
| pH adjusted to 5.8 | |

TABLE 4

10x B5 Salts

| Component | Concentration |
|---|---|
| Ammonium Sulfate | 134 mg/L |
| Boric Acid | 3 mg/L |
| Calcium Chloride · 2H$_2$O | 150 mg/L |
| Cobalt Chloride · 6H$_2$O | 0.025 mg/L |
| Cupric Sulfate · 5H$_2$O | 0.025 mg/L |
| EDTA (Disodium Salt) · 2H$_2$O | 37.3 mg/L |
| Ferrous Sulfate · 7H$_2$O | 27.8 mg/L |
| Magnesium Sulfate · 7H$_2$O | 250 mg/L |
| Manganese Sulfate · H$_2$O | 10 mg/L |
| Molybdic Acid (Sodium Salt) · 2H$_2$O | 0.25 mg/L |
| Potassium Iodide | 0.75 mg/L |
| Potassium Nitrate | 2500 mg/L |
| Sodium Phosphate Monobasic · H$_2$O | 150 mg/L |
| Zinc Sulfate · 7H$_2$O | 2 mg/L |

TABLE 5

100x B5 Vitamins + Inositol

| Component | Concentration |
|---|---|
| Inositol | 10 g/L |
| Nicotinic Acid | 0.1 g/L |
| Pyridoxine-HCL | 0.1 g/L |
| Thiamine-HCL | 1 g/L |
| pH adjusted to 5.6 | |

B. Bombardment Conditions

Tungsten or gold particles are sterilized for use as microcarriers in bombardment experiments. Gold particles ((1.4 mg, enough for 5 bombardments) 0.6 micron gold particles (#1652262, Bio-Rad Laboratories) are sterilized with 100% ethanol. Immediately prior to use, particles are sedimented by centrifugation, washed with 2 to 3 washes of sterile deionised distilled water, vortexed and centrifuged between each wash. Washed particles are resuspended in 50 µl of sterile water.

To the 50 µl of sterile gold particles is added 10 µl of a 1 ug/µl solution containing pCGN6408 DNA in TE buffer. Also added was 50 µl of 2.5M CaCl2 and 20 µl of 0.1M spermidine free base. The particles are shaken for 10 minutes at 4° C., centrifuged washed 4 times in 100% ethanol. The final suspension in absolute ethanol is 30 µl. Five microliters of this suspension is loaded on a flying disc for use in particle bombardments.

Dark green leaves, about ¾ expanded, approximately 3 to 4 cm in length, are chosen for bombardment from the source plants. Leaves are cut, leaving no petiole and placed with the abaxial side against the Shooting medium (Table 6) in petri dishes. Immediately before shooting leaves are gently pressed flat in contact with the medium.

TABLE 6

Shooting Medium

| Component | Concentration |
|---|---|
| 10x B5 Salts (Table 4) | 1x |
| 100x B5 Vitamins + Inositol (Table 5) | 1x |
| Sucrose | 30 g/L |
| BAP | 1 mg/L |
| Phytagar | 6 g/L |
| pH adjusted to 5.8 | |

Transformation by particle bombardment is carried out using the PDS 1000 Helium gun (Bio Rad, Richmond, Calif.) using a modified protocol described by the manufacturer.

The flying disc was placed in a launch ring, which is screwed into a sleeve with a metal stopping screen on a retainer ring 1 cm below the launch ring. The flying disc had an effective flight distance of 1 cm. Leaves are placed on the second platform from the bottom of the gun, 12 cm from the stopping screen and bombarded using a 1100 p.s.i. rupture disk.

C. Regeneration of Transformed Shoot

After bombardment, leaves are left on the shooting medium plates and are sealed with ¼" Microporeä tape (3M Health Care, St. Paul, Minn. 555144) and placed in the culture room at 21° C. for two days with light conditions of 90 photons/meter$^2$/sec and a photoperiod of 16 hours light. After two days, the leaves are removed from the media and cut into approximately 1 cm squares. The squares are placed abaxial side against Brassica Regeneration medium (Table 7) supplemented with 20 mg/l spectinomycin. After seven days on Brassica Regeneration medium leaf pieces are moved to Shoot development medium (Table 8) supplemented with 20 mg/l spectinomycin, abaxial side against the medium. After two weeks, the leaf pieces are moved to fresh Shoot development medium containing 20 mg/l spectinomycin.

Both bleached (purple/white) shoots and green shoots regenerated about 6 to 8 weeks after bombardment. Green shoots, approximately 0.25 to 0.5 cm in height, and a small part of the explant are moved to fresh Shoot development medium with 20 mg/l spectinomycin. A green shoot (99-A), elongated to approximately 1 cm in height and was removed from the explant and placed on shoot elongation medium (Table 9) plus 20 mg/l spectinomycin. At 2 cm in height the shoot is placed on rooting medium supplemented with 20 mg/l spectinomycin.

TABLE 7

Regeneration Medium

| Component | Concentration |
|---|---|
| 10x B5 Salts (Table 4) | 1x |
| 100x B5 Vitamins + Inositol (Table 5) | 1x |
| AgNO$_3$ | 3 mg/L |
| Sucrose | 30 g/L |
| N6-benzylaminopurine (BAP) | 5 mg/L |
| Naphthaleneacetic acid (NAA) | 5 mg/L |
| Phytagar | 6 g/L |
| pH adjusted to 5.8 | |

TABLE 8

Shoot Development Medium

| Component | Concentration |
|---|---|
| 10x B5 Salts (Table 4) | 1x |
| 100x B5 Vitamins + Inositol (Table 5) | 1x |
| BAP | 3 mg/L |
| Zeatin | 1 mg/L |
| Sucrose | 10 g/L |
| Phytagar | 7 g/L |
| pH adjusted to 5.8 | |

TABLE 9

Shoot Elongation Medium

| Component | Concentration |
|---|---|
| 10x B5 Salts (Table 4) | 1x |
| 100x B5 Vitamins + Inositol (Table 5) | 1x |
| Sucrose | 10 g/L |
| Phytagar | 6 g/L |
| pH adjusted to 5.8 | |

TABLE 10

Rooting Medium

| Component | Concentration |
|---|---|
| 10x B5 Salts (Table 4) | 1x |
| 100x B5 Vitamins + Inositol (Table 5) | 1x |
| Sucrose | 10 g/L |
| IBA | 1 mg/L |
| Phytagar | 6 g/L |
| pH adjusted to 5.8 | |

D. Regeneration of Homoplasmic Shoots

Leaves are removed from the heteroplasmic shoot from shot 99, cut into 0.5 cm pieces and placed abaxial side against the medium on Regeneration medium supplemented with 20 mg/l spectinomycin. After seven days on Brassica Regeneration medium leaf pieces are moved to Shoot development medium with 20 mg/l Spectinomycin, abaxial side against the medium. Two weeks later the leaf pieces were moved to fresh to Shoot development medium plus 20 mg/l spectinomycin. Green shoots regenerated about 2 to 3 weeks after leaves were cut up. Green shoots and a small part of the explant were moved to fresh to Shoot development medium plus 20 mg/l spectinomycin at approximately 0.25 to 0.5 cm in height. At approximately 1 cm in height, shoots were cut off the explant and transferred to shoot elongation medium plus 20 mg/l spectinomycin. At 2 cm in height shoots were placed on rooting medium (table 10) containing 20 mg/l spectinomycin.

Example 3

Analysis of Transplastomic Plants

Transformed plants selected for marker aadA marker gene expression are analyzed to determine whether the entire plastid content of the plant has been transformed (homoplastic transformants). Typically, following two rounds of shoot formation and spectinomycin selection, approximately 50% of the transgenic plantlets which are analyzed are homoplastic, as determined by Southern blot analysis of plastid DNA. Heteroplasmic plantlets are selected for further subculturing to obtain homoplasmic lines.

Genomic DNA can be isolated from transformed *Brassica* plants, electrophoresed, and transferred to filters as generally described by Svab et al. ((1993), *Proc Natl Acad Sci*, 90:913–917). Plastid transformants are identified by Southern analysis after digestion of total DNA with StuI restriction enzyme.

Figure 2:
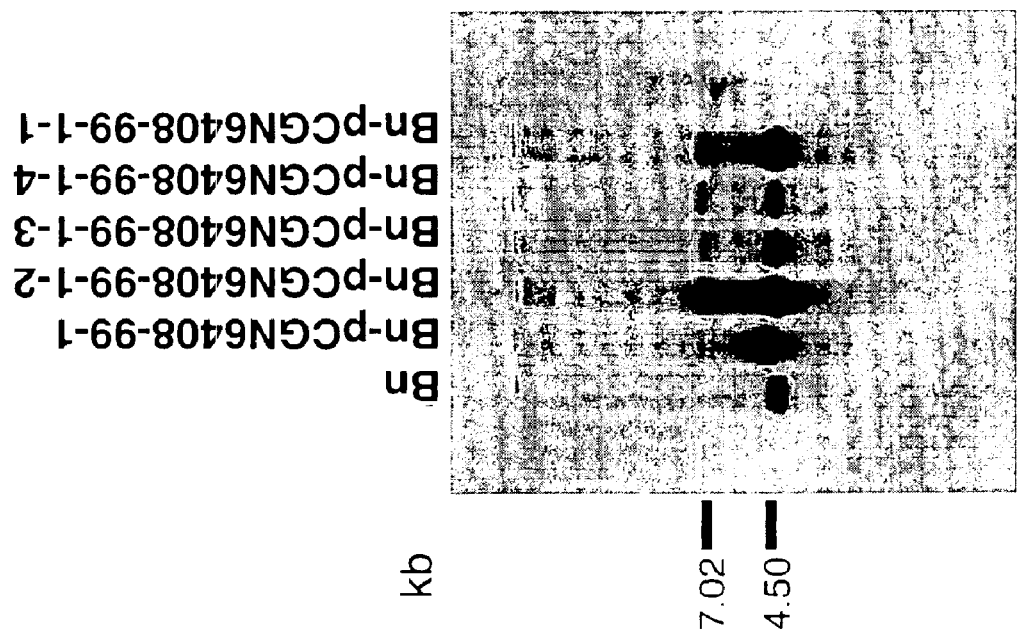
FIG. 2 provides the results of Southern hybridizations for nontransformed (wild-type, Bn) and transplastomic *Brassica* lines.

Total DNA is extracted from leaves using plant DNAzol Reagent (GIBCO BRL), digested with StuI, electrophoresed on 0.7% agarose gels and transferred to nylon membranes (Amersham) using standard techniques. Blots are probed using Rapid Hybridization buffer (Amersham) using $^{32}$P-labeled PCR amplified DNA probe obtained with primers SC177 and SC178 from pCGN6408. The probed region comprises the entire NotI-SacI flank sequence of *Brassica* plastid vector pCGN6408 (FIG. 1). This probe detects a 4.50 kb fragment in wild type *Brassica napus* 212/86 DNA and a 7.02 kb transgenic fragment in Bn-pCGN6408-1 line and its secondary regenerates Bn-pCGN6408-1-1, Bn-pCGN6408-1-2, Bn-pCGN6408-1-3 and Bn-pCGN6408-1-4. The presence of both wild-type size and transgenic fragments in the transgenic lines indicates that they are heteroplasmic for the transformed plastid DNA (FIG. 2).

Figure 3:
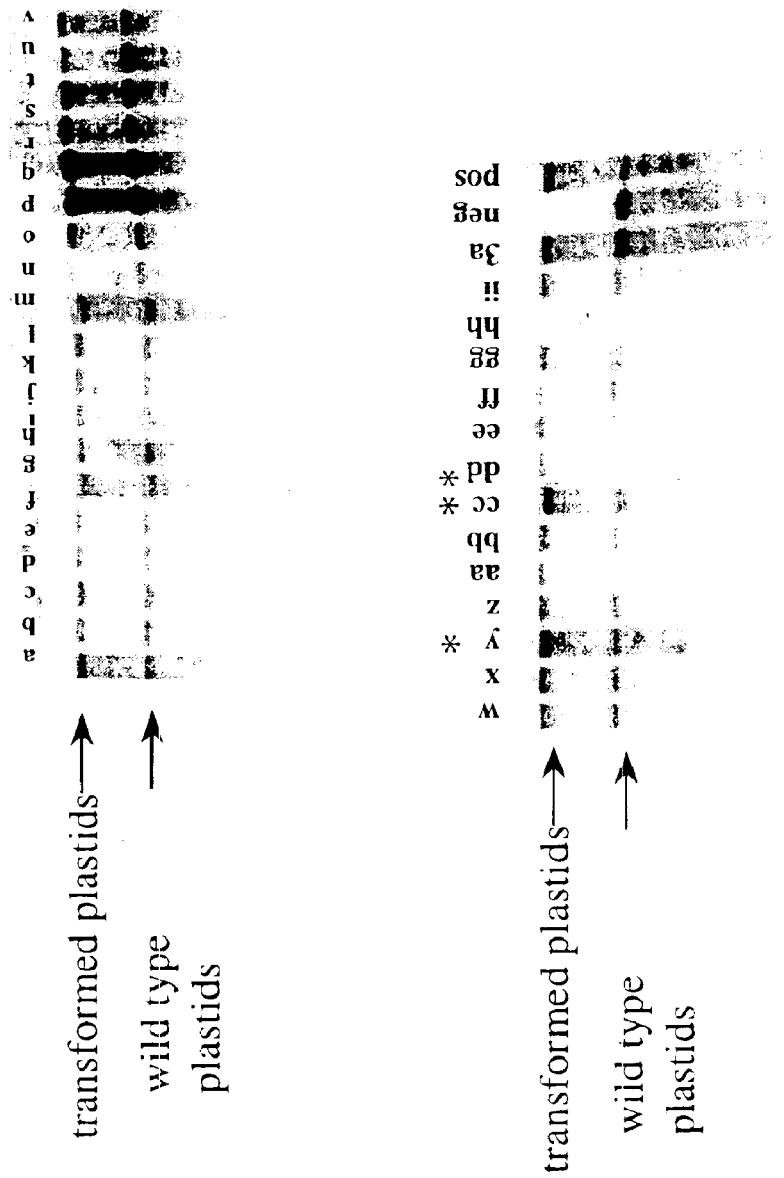
FIG. 3 provides Southern Hybridization results for subsequent rounds of shoots, lines 6408 99-1Y, cc, and dd are about 80% homoplasmic.

Homoplasmic plants are obtained through further subculturing using excised leaf tissue for regeneration of plants using the regeneration methods described in Example 2C. Homoplasmic *Brassica* plants are identified using Southern blot hybridizations as described above and selecting lines demonstrating a single hybridizing fragment of 7.02 kb corresponding to the transplastome. FIG. 3 provides Southern Hybridization results for subsequent lines. Lines 6408 99-1Y, cc, and dd are about 80% homoplasmic.

Example 4
Analysis of GFP Expression

Leaves from heteroplasmic shoot (Bn-6408-99-1) and an nontransformed control shoot are removed and sliced tangentially. Prepared leaves are observed with a Nikon Labophot fluorescent microscope and photos are taken with a Nikon UFX-II photomicrography unit.

Visual observation of the prepared tissues reveals fluorescence from the chloroplasts in the guard cells of stomates under blue light. Thus, demonstrating GFP expression from the *Brassica* plant cell plastid.

Quantitative analysis of GFP expression can be determined using Western Immunoblot analysis. For example, total soluble protein can be extracted from frozen or frozen leaf tissue by grinding 250 mg tissue in 250 µl of PBS buffer (1 mM $KH_2PO_4$, $Na_2HPO_4$, 0.137M NaCl, 2.7 mM KCl pH 7.0) containing protease inhibitors. The homogenate is centrifuged for 5 minutes, and the supernatant is transferred to a fresh tube. The concentration of the protein in the supernatant is determined using a protein concentration assay (BioRad, Richmond, Calif.).

Extracted total protein is electrophoresed on a 4–20% SDS-PAGE gel (Sigma, St Louis, Mo.), and transferred to PVDF membrane in 1×SDS-PAGE buffer (Maniatis et al. 1989, Cold Spring Harbor Press). Standards of quantitated purified GFP protein are used to quantify the expression of the GFP as expressed in the plant plastid.

Western hybridizations are performed as described in Staub and Maliga (1993) *EMBO Journal*, 12(2) 601–606, except using antibodies raised to GFP. PVDF membranes containing the transferred electrophoresed protein are incubated in a blocking solution of PBS buffer containing 0.05% Tween-20 (PBS-T) and 5% milk overnight at 4° C. The membranes are then incubated in a solution of PBS-T containing 1% milk and a primary antibody raised in goats to GFP for 2 hours at room temperature. The membranes are washed three times in a solution of PBS-T containing 0.1% milk, each wash for 5 minutes at room temperature. The membranes are then incubated in a solution of PBS-T containing 1% milk and sheep anti-goat antibody for 1 hour at room temperature, and washed again in PBS-T containing 0.1% milk, three times for 10 minutes at room temperature. A final wash using only PBS-T is performed before developing the membranes using, for example, a nonradioactive detection kit (ECL, Amersham).

Thus, the above results demonstrate that the methods provided in the present invention allow for the transformation of *Brassica* plant cell plastids.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications can be practiced within the scope of the appended claim.

What is claimed is:

1. A method for the transformation of a Brassica plant cell comprising:
introducing into plastids of said Brassica plant cell a construct comprising a promoter functional in a Brassica plant plastid operably associated with a nucleic acid sequence from Bacillus thuringiensis encoding a crystal protein providing for resistance to insects and a transcriptional terminator functional in a Brassica plant cell plastid, and flanking regions of homology to the *Brassica* plastid genome comprised of a pair of regions of a *Brassica* chloroplast genome of a size from about 1 kb to about 2.5 kb and which comprise or reside within a region identified by PCR amplification at 94 degrees C. for 4 minutes, 30 cycles of 94 degrees C. for 30 seconds, 50 degrees C. for 30 seconds, 72 degrees C. for 1 minute 45 seconds, with a final extension at 72 degrees C. for 7 minutes using SEQ ID NOS 3–4 and SEQ ID NOS 5–6 as primers, whereby said flanking regions cause the integration of the construct into the plastid genome of said *Brassica* plant cell, and selecting *Brassica* plant cells having plastids containing said construct.

2. A method for the transformation of a *Brassica* plant cell comprising:

introducing into plastids of said *Brassica* plant cell a construct comprising a promoter functional in a *Brassica* plant plastid operably associated with a nucleic acid sequence encoding a human biological protein and a transcriptional terminator functional in a *Brassica* plant cell plastid, and flanking regions of homology to the *Brassica* plastid genome comprised of a pair of regions of a *Brassica* chloroplast genome of a size from about 1 kb to about 2.5 kb and which comprise or reside within a region identified by PCR amplification at 94 degrees C. for 4 minutes, 30 cycles of 94 degrees C. for 30 seconds, 50 degrees C. for 30 seconds, 72 degrees C. for 1 minute 45 seconds, with a final extension at 72 degrees C. for 7 minutes using SEQ ID NOS 3–4 and SEQ ID NOS 5–6 as primers, whereby said flanking regions cause the integration of the construct into the plastid genome of said *Brassica* plant cell, and selecting *Brassica* plant cells having plastids containing said construct.

3. The method according to claim 1 further comprising regenerating a mature *Brassica* plant containing transformed plastids from said *Brassica* plant cells.

4. The method according to claim 1 wherein said *Brassica* plant cell is a *Brassica napus* plant cell.

5. The method according to claim 1 wherein said *Brassica* plant cell comprises a leaf cell.

6. A *Brassica* plant cell obtained by the method of claim 1.

7. A *Brassica* plant, plant seed or plant part, or progeny thereof, containing a *Brassica* plant cell according to claim 6.

8. A fertile *Brassica* plant having plastids containing a heterologous construct, wherein said construct comprises as operably associated components in the 5' to 3' direction of transcription, a promoter functional in a plant cell plastid, a nucleic acid sequence from *Bacillus thuringiensis* encoding a crystal protein providing for resistance to insects and a transcriptional terminator functional in a plant cell plastid whereby said construct is integrated into the plastid genome of said *Brassica* plant through regions of homology to the *Brassica* plastid genome flanking the heterologous construct, said regions of homology comprised of a pair of regions of a *Brassica* chloroplast genome of a size from about 1 kb to about 2.5 kb and which comprise or reside within a region identified by PCR amplification at 94 degrees C. for 4 minutes, 30 cycles of 94 degrees C. for 30 seconds, 50 degrees C. for 30 seconds, 72 degrees C. for 1 minute 45 seconds, with a final extension at 72 degrees C. for 7 minutes using SEQ ID NOS 3–4 and SEQ ID NOS 5–6 as primers.

9. The *Brassica* plant according to claim 8 wherein said *Brassica* plant is *Brassica napus*.

10. The *Brassica* plant according to claim 8 wherein said plastids containing the heterologous construct are present in the leaf cells of said *Brassica* plant.

11. A *Brassica* seed or *Brassica* plant part, or progeny thereof, derived from a *Brassica* plant according to claim 8, each containing said heterologous construct.

12. The *Brassica* plant of claim 8 wherein the regions of homology include the trnV-rps7/12 intergenic region and the heterologous construct is integrated into the corresponding location in the *Brassica* plastid genome.

13. The *Brassica* plant of claim 8 wherein the regions of homology are nucleotides 1–2432 and 4960–7454 of SEQ ID NO:19.

14. The method according to claim 2 further comprising regenerating a mature *Brassica* plant containing transformed plastids from said *Brassica* plant cells.

15. The method according to claim 2 wherein said *Brassica* plant cell is a *Brassica napus* plant cell.

16. The method according to claim 2 wherein said *Brassica* plant cell comprises a leaf cell.

17. A *Brassica* plant cell obtained by the method of claim 2.

18. A *Brassica* plant, plant seed or plant part, or progeny thereof, containing a *Brassica* plant cell according to claim 17.

19. A fertile *Brassica* plant having plastids containing a heterologous construct, wherein said construct comprises as operably associated components in the 5' to 3' direction of transcription, a promoter functional in a plant cell plastid, a nucleic acid sequence encoding a human biological protein and a transcriptional terminator functional in a plant cell plastid whereby said construct is integrated into the plastid genome of said *Brassica* plant through regions of homology to the *Brassica* plastid genome flanking the heterologous construct, said regions of homology comprised of a pair of regions of a *Brassica* chloroplast genome of a size from about 1 kb to about 2.5 kb and which comprise or reside within a region identified by PCR amplification at 94 degrees C. for 4 minutes, 30 cycles of 94 degrees C. for 30 seconds, 50 degrees C. for 30 seconds, 72 degrees C. for 1 minute 45 seconds, with a final extension at 72 degrees C. for 7 minutes using SEQ ID NOS 3–4 and SEQ ID NOS 5–6 as primers.

20. The *Brassica* plant according to claim 19 wherein said *Brassica* plant is *Brassica napus*.

21. The *Brassica* plant according to claim 19 wherein said plastids containing the heterologous construct are present in the leaf cells of said *Brassica* plant.

22. A *Brassica* seed or *Brassica* plant part, or progeny thereof, derived from a *Brassica* plant according to claim 19, each containing said heterologous construct.

23. The *Brassica* plant of claim 19 wherein the regions of homology include the tmV-rps7/12 intergenic region and the heterologous construct is integrated into the corresponding location in the *Brassica* plastid genome.

24. The *Brassica* plant of claim 19 wherein the regions of homology are nucleotides 1–2432 and 4960–7454 of SEQ ID NO:19.

* * * * *

UNITED STATES PATENT AND TRADEMARK OFFICE
CERTIFICATE OF CORRECTION

PATENT NO. : 6,891,086 B2  
DATED : May 10, 2005  
INVENTOR(S) : Chaudhuri et al.

It is certified that error appears in the above-identified patent and that said Letters Patent is hereby corrected as shown below:

<u>Column 34,</u>  
Line 17, "tmV-rps7/12" should read -- trnV-rps7/12 --.

Signed and Sealed this

Thirteenth Day of December, 2005

JON W. DUDAS  
*Director of the United States Patent and Trademark Office*